United States Patent [19]

Zeiler

[11] Patent Number: 5,344,975
[45] Date of Patent: Sep. 6, 1994

[54] PROCESS FOR PRODUCTION OF LOWER ALKANOIC ACIDS

[75] Inventor: Andrew G. Zeiler, South Haven, Mich.

[73] Assignee: Wyckoff Chemical Company, Inc., South Haven, Mich.

[21] Appl. No.: 116,363

[22] Filed: Sep. 3, 1993

[51] Int. Cl.$^5$ .................. C07B 53/00; C07C 53/08
[52] U.S. Cl. .................. 562/606; 562/607; 562/608
[58] Field of Search .................. 562/606, 607, 608

[56] References Cited

U.S. PATENT DOCUMENTS

| | | | |
|---|---|---|---|
| 2,523,490 | 9/1950 | Adams et al. | 260/513 |
| 3,579,297 | 5/1971 | Ekblom | 562/608 |
| 3,661,950 | 5/1972 | Larkin et al. | 260/413 |
| 3,786,086 | 1/1974 | Skov et al. | 562/608 |
| 4,127,604 | 11/1978 | Chignac et al. | 562/606 |
| 4,215,225 | 7/1980 | Funk et al. | 562/606 |
| 4,317,925 | 3/1982 | Weber et al. | 562/531 |
| 5,101,070 | 3/1992 | Yamamoto et al. | 562/606 |

FOREIGN PATENT DOCUMENTS 136499  11/1987  Poland .

OTHER PUBLICATIONS

B. S. Furniss et al., Vogel's Textbook of Practical Organic Chemistry, III, 133/134, pp. 494–495 (Longman, London & New York, 4th ed.) (1980).
Dario Landini et al., "Acid Hydrolysis of Carboxylic Esters in a Two-Phase System . . . ", J. Org. Chem. 1982, vol. 47, pp. 154–156 (1982).
B. Loev, "Acid Catalysed 'Hydrolysis' of Esters," Chemistry and Industry, pp. 193–194 (Feb. 1, 1964).

*Primary Examiner*—Arthur C. Prescott
*Attorney, Agent, or Firm*—Baker & Daniels

[57] ABSTRACT

A process for production of lower alkanoic acids. A reaction mixture comprising a substituted malonic acid, an acid catalyst, and a limited amount of water is heated to a temperature sufficient to hydrolyze and decarboxylate the ester. The reaction mixture is maintained at the temperature by periodic addition of limited amounts of water, and the reaction is continued for a period of time sufficient to remove substantially all of the alcohol and carbon dioxide generated by the hydrolysis reaction, thereby converting substantially all of the ester to alkanoic acid. The process is particularly useful for the production of valproic acid.

28 Claims, No Drawings

PROCESS FOR PRODUCTION OF LOWER ALKANOIC ACIDS

BACKGROUND OF THE INVENTION

The present invention relates generally to a process for the production of alkanoic acids, and particularly to a process for the production of lower alkanoic acids by acid catalyzed hydrolysis and decarboxylation of substituted malonic esters without the use of solvents.

Many lower alkanoic acids are known to be useful for their pharmacological properties, as pharmacological intermediates and as chemical intermediates. A particularly important lower alkanoic acid is valproic acid, $(CH_3CH_2CH_2)_2CHCOOH$, which is widely used in the pharmaceutical industry for its anticonvulsant and antiepileptic properties.

A well-known process for preparing alkanoic acids involves the hydrolysis and decarboxylation of malonic esters. The malonic ester is saponified with aqueous sodium hydroxide to form an aqueous solution of the disodium salt and ethanol. The salt solution is treated with a strong mineral acid to produce a mineral acid sodium salt and to precipitate the solid dicarboxylic acid. The dicarboxylic acid is isolated from the solution by conventional separation procedures, such as filtration or extraction, and the sodium salt is discarded as waste. The isolated acid is dried and heated to a temperature sufficient to cause decarboxylation to occur. This procedure is lengthy, requires numerous steps, generates waste, and is equipment intensive.

Acid catalyzed hydrolysis of carboxylic esters has certain advantages over the classical procedure described above. For example, the production of the intermediate sodium salt and the resultant generation of waste material is avoided. The dicarboxylic acid isolation step is eliminated and, in some instances, the acid catalyst may be recovered for reuse. Nonetheless, certain problems persist in the known acid hydrolysis procedures. For example, the rate of the reaction is slow, and it is often difficult to drive the hydrolysis to completion due to the competing reverse reaction of esterification. Additionally, many of these procedures are equipment intensive and require substantial excesses of some of the ingredients.

Several methods have been described in the literature as attempts to overcome the difficulties encountered in the acid hydrolysis procedures. For example, German Patent 30 45 102 discloses a gas phase reaction for the production of substituted acetic acids and/or their esters. Only partial conversion of the acid is accomplished by this method, and severe conditions are required for the reaction.

Another process utilizing acid hydrolysis was disclosed by B. Loev in *Chemistry and Industry*, (London), 1964, p. 193. This reference teaches acid catalyzed hydrolysis of esters using large amounts of acetic or formic acid as a solvent in the presence of 100 mole % of a mineral acid, such as methanesulfonic acid. In order to recover the carboxylic acid product, it is necessary to isolate the product from the reaction mixture by filtration or extraction, or by heating to remove the volatile materials, and thereafter recrystallizing or distilling the residue. The mineral acid may not normally be reclaimed from the solvent for reuse in this procedure, and halogenated hydrocarbon by-products are generated as waste when the mineral acid is hydrochloric or hydrobromic acid.

Landini and Rolla, *J. Org. Chem.*, 1982, Vol. 47, p. 154–157, disclose a process for acid hydrolysis of carboxylic esters in a two-phase system in the presence of catalytic amounts of a quaternary onium salt. This hydrolysis proceeds at room temperature in the presence of a large excess of a strong mineral acid, such as hydrobromic acid, sulfuric acid or hydrochloric acid. Disadvantages of this process are that a two-phase system is required, and that the reaction must proceed in the presence of the large excess of the mineral acid. Halogenated hydrocarbons are also produced as by-products by this process when hydrobromic and hydrochloric acids are used.

Vogel, *Textbook of Practical Organic Chemistry*, Fourth Ed., Longman Group Limited (1978), p. 194–5, teaches a method for acid hydrolysis of some highly oxygenated malonic esters by refluxing with a large molar excess of aqueous hydrochloric acid. The ethanol generated by the reaction is removed by distillation as fast as it is formed, without undue removal of water, in order to drive the hydrolysis reaction to completion. Since the esters utilized in this process are highly oxygenated, these esters are soluble in hot water, and the intermediate dicarboxylic acids are decarboxylated at 100° C. The carboxylic acid is recovered by evaporating the solution to dryness under reduced pressure, redissolving in water, and again evaporating to dryness to remove the excess hydrochloric acid. The residue is thereafter dissolved in water, passed through a column of decolorizing carbon, and again evaporated to dryness under reduced pressure. The dried residue is ground to a fine powder, mixed with ether, filtered, washed with ether and dried. This process is lengthy and equipment intensive, requires the use of a large molar excess of strong acid solvent, and cannot be used with hydrophobic starting esters.

Another method for preparing valproic acid is disclosed in Polish Patent 136,499. Dipropylmalonic acid is decarboxylated by heating at 140°–145° C. in the presence of 2 wt % valproic acid, the valproic acid acting as a decarboxylation catalyst. In this process, the diacid must be prepared and isolated by the classical method prior to the decarboxylation.

U.S. Pat. No. 5,101,070 discloses a process for producing valproic acid from an acetoacetic acid ester by a three-step process. The first step involves producing a 2,2-dipropyl acetoacetic acid ester from an acetoacetic acid ester in the presence of a basic catalyst. In the second step the 2,2-dipropyl acetoacetic acid ester is deacetylated with an alcohol in the presence of a basic catalyst to give a valproic acid ester. The third step involves hydrolyzing the valproic acid ester. In the hydrolysis step, the valproic acid ester is heated under reflux at elevated temperatures for 2–5 hours. The pH of the reaction solution is adjusted to 9 to 10, and the solution is extracted with an organic solvent. The pH of the aqueous layer is adjusted to about 2, and the organic layer containing the valproic acid is separated. This process is lengthy and generates waste as a result of the neutralization step.

U.S. Pat. No. 3,661,950 discloses a process for producing alkanoic acids having between 1 and 20 carbon atoms from nitroketones. A vicinal nitroketone is contacted under nonaqueous conditions with a catalyst comprising a sulfonic acid cation exchange resin. The alkanoic acid is recovered by separating the catalyst, and then cooling the reaction mixture to a temperature below 100° C. The solid catalyst is recovered by filtration. The alkanoic acid and hydrocarbons are thereafter separated by distillation. The use of nitro compounds of the type utilized in this process can be hazardous due to the generally higher toxicity of these compounds when compared to alkanes. Also, the nitro compounds are more unstable than conventional reactants used for producing alkanoic acids. Since fractional distillation is required for the separation, it is also expected that the purity of the final product would be lower than desired.

The known processes for the production of lower alkanoic acids, such as valproic acid, generally require either expensive starting ingredients, lengthy and time consuming procedures and/or a wide array of laboratory equipment in order to perform the process. They also generate waste in the form of by-products and frequently require large excesses of reaction ingredients. Some of the processes are not effective when hydrophobic starting materials are hydrolyzed.

Accordingly, it is desired to provide a process for the production of lower alkanoic acids that is cost effective, provides a satisfactory yield of product, does not generate a significant amount of solid waste, and enables the alkanoic acid product to be produced in one reactor in an uninterrupted operation.

SUMMARY OF THE INVENTION

The problems of the prior art are addressed by the present invention wherein a process for the production of lower alkanoic acids is provided. The invention comprises a process for the production of lower alkanoic acids by acid-catalyzed hydrolysis and decarboxylation of substituted malonic esters without the use of solvents.

The present invention, in one form thereof, provides a process for production of alkanoic acids of the formula

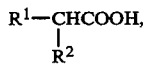

wherein $R^1$ is an alkyl group containing from about 2 to 10 carbon atoms, or a branched alkyl, cycloalkyl or aryl group containing from about a 3 to 10 carbon atoms, and $R^2$ is H, an alkyl group containing from about 1 to 10 carbon atoms, or a branched alkyl, cycloalkyl or aryl group containing from about 3 to 10 carbon atoms. The process comprises heating a reaction mixture comprising a substituted malonic ester of the formula

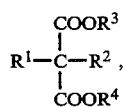

wherein $R^1$ and $R^2$ represent alkyl, branched alkyl, aryl or cycloalkyl groups as described above, and $R^3$ and $R^4$ represent lower alkyl groups containing from about 1 to about 4 carbon atoms, in the presence of an acid catalyst and water to a temperature sufficient to hydrolyze and decarboxylate the ester. The acid catalyst is at least partially soluble in the ester. The reaction mixture is maintained at this temperature for a period of time sufficient to drive the hydrolysis reaction substantially to completion, and to remove substantially all of the alcohol and carbon dioxide generated by the hydrolysis and decarboxylation from the reaction mixture.

The invention further comprises, in another form thereof, a process for production of alkanoic acids wherein a reaction mixture is prepared which consists essentially of a substituted malonic ester, an acid catalyst and water. The acid catalyst is at least partially soluble in the ester at temperatures above 100° C. and comprises an arylsulfonic acid, an alkylsulfonic acid or a mixture of the two. The amount of water in the reaction mixture is intentionally limited so that there is insufficient water present for complete extraction of the acid catalyst from the ester into the water. The reaction mixture is heated to a temperature sufficient to hydrolyze and decarboxylate the ester. The reaction mixture is maintained at this temperature by periodically adding a limited amount of water to the reaction mixture. The heating is continued at this temperature for a period of time sufficient to remove substantially all of the alcohol and carbon dioxide generated by the hydrolysis and decarboxylation, thereby converting substantially all of the ester to alkanoic acid. The alkanoic acid is then isolated by separating the catalyst from the reaction mixture.

The present invention comprises, in accordance with another embodiment thereof, a process for preparing valproic acid in which a reaction solution is prepared in a reflux flask equipped with a distillation column. The reaction solution consists essentially of a substituted malonic ester selected from the group consisting of diethyl dipropylmalonate and diethyl buthylmethylmalonate, an acid catalyst selected from the group consisting of an arylsulfonic acid and an alkylsulfonic acid and mixtures thereof, and water. The acid catalyst is at least partially soluble in the ester at temperatures in excess of 100° C. The water is limited to an amount such that the acid catalyst cannot be completely extracted from the ester into the water. The reaction mixture is heated to a temperature between about 100°–155° C. to hydrolyze and decarboxylate the ester. The reaction mixture is maintained at the desired temperature by periodic addition of a limited amount of water to the flask, and the heating is continued for a period of time sufficient to remove substantially all of the ethanol and carbon dioxide generated by the hydrolysis and decarboxylation of the ester, thereby converting substantially all of the ester to valproic acid. The catalyst is then separated from the valproic acid. The valproic acid may be further purified by vacuum distillation.

DETAILED DESCRIPTION OF THE INVENTION

The present invention provides a process for the production of alkanoic acids by acid catalyzed hydrolysis and decarboxylation of substituted malonic esters. The process is particularly useful for the production of alkanoic acids of the formula:

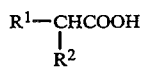

wherein $R^1$ is an alkyl, branched alkyl, cycloalkyl or aryl group containing from about 2 to 10 carbon atoms, and $R^2$ is H or an alkyl, branched alkyl, cycloalkyl or aryl group containing from about 1 to 10 carbon atoms. It is preferred that the total number of carbon atoms $R^1$ and $R^2$ not be greater than about 16 and most preferred that it not be greater than about 10, in order to maintain the desired solubility of the acid catalyst in the ester.

Alkanoic acids in this range find particular utility in the pharmaceutical industry and as pharmacological and chemical intermediates. Valproic acid, (CH₃CH₂CH₂)₂CHCOOH (also known as 2-propylpentanoic acid, 2-propylvaleric acid and di-n-propylacetic acid) is a well known anticonvulsant and an antiepileptic agent.

The process of the present invention comprises a procedure wherein the hydrolysis and decarboxylation reactions take place in a single reaction vessel, or "pot". The hydrolysis reaction of the substituted malonic esters occurs in the presence of a small amount of a recyclable strong acid catalyst, and water. The acid catalyst must be at least partially soluble in the diester at temperatures above 100° C. The water content in the reaction vessel must be limited in order to prevent the undesired extraction of the catalyst from the diester into a water phase.

The substituted malonic esters utilized in the invention have the general formula:

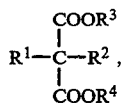

wherein $R^1$ and $R^2$ represent alkyl, branched alkyl, aryl or cycloalkyl groups as described above, and $R^3$ and $R^4$ represent lower alkyl groups containing from about 1 to about 4 carbon atoms.

Alkyl substituted malonic esters such as diethyl dipropylmalonate and diethyl butylmethylmalonate are particularly preferred starting materials for the production of lower alkanoic acids. Other preferred substituted malonic esters are dimethyl dipropylmalonate, dimethyl butylmethylmalonate and phenylmalonic esters. Various other alkyl, branched alkyl, cycloalkyl and aryl substituted malonic esters fitting within the above formula may also be utilized. The methyl and ethyl esters of the malonic acids are the most preferred esters in the inventive process. Diethyl dipropylmalonate and dimethyl dipropylmalonate are preferred starting materials for the production of valproic acid.

Unlike many of the prior art processes wherein large amounts of solvent are required, the malonic ester itself acts as the solvent in the inventive process. Thus the need for the large excess of mineral acids typical of many prior art processes has been eliminated, along with the necessity to include additional separation steps in the process to separate the mineral acid and by-products from the reaction product.

The inventive process is particularly useful when the starting materials are esters of a substantially hydrophobic nature, since acid-catalyzed hydrolysis of hydrophobic esters is difficult by existing methods. When utilizing hydrophobic esters as starting materials, the solubility of the catalyst in the diester is readily maintained under the conditions of the reaction. Although the process is particularly beneficial when used with hydrophobic starting materials, the inventive process may also be used with hydrophilic esters.

The catalyst for the reaction comprises an arylsulfonic acid, an alkylsulfonic acid or a combination of the two. These acids are at least partially soluble in the malonic esters at temperatures above 100° C. Although a wide variety of arylsulfonic acids and alkylsulfonic acids may be utilized, sulfonic acids such as methanesulfonic acid, p-toluenesulfonic acid monohydrate and benzenesulfonic acid are particularly preferred for use in the reaction.

The one pot procedure for preparation of lower alkanoic acids according to the process of the present invention is described in further detail hereinbelow. A mixture of the substituted malonic ester, the acid catalyst and a small amount of water is added to a reflux flask. The reflux flask is equipped with a distillation column packed with Raschig rings in the conventional manner. Approximately 1–200 mole % of acid catalyst may be utilized; however it is preferred that the catalyst be in the range of about 15–61 mole %, and most preferred that it be in the range of about 15–20 mole %. As stated, the water content in the reaction vessel is limited to an amount insufficient for complete extraction of the acid catalyst from the ester into the water. The amount of water required is controlled by the amount used for hydrolysis and the amount needed to establish the proper boiling point of the system. The boiling point, and thus the reaction temperature, is determined by the amount of water present.

Heat is applied to the reaction vessel, and the reaction mixture is heated to reflux. Although the reaction may be carried out within a temperature range of about 100°–180° C., it is preferred that the temperature range be between about 100°–155° C., and most preferred that the reaction be carried out between about 120°–140° C. It is important that the temperature of the reaction mixture be sufficiently high to initiate the hydrolysis reaction. The reaction may be carried out at pressures between about 0.2–1.5 Atm, although it is preferred that the reaction proceed at atmospheric pressure.

The heating of the reaction vessel is maintained at the chosen temperature so that the alcohol formed by the hydrolysis reaction is continuously removed from the reaction mixture by distillation. In this manner, the hydrolysis reaction is driven to completion, and the competing reverse reaction of esterification is prevented. During the course of the reaction at this elevated temperature, additional limited amounts of water are periodically added to the reaction vessel to maintain the boiling point of the mixture within the desired temperature range. The ester undergoes decarboxylation, and the carbon dioxide generated by this reaction is also removed from the mixture via the distillation column. The pot is maintained at the reaction temperature by controlling the boiling point via the periodic addition of the limited amounts of water. It is important that the additional amounts of water added to the pot be limited in the same manner as the initial amount of water, that is, to an amount such that the catalyst cannot be fully extracted into the water phase.

After the evolution of the alcohol and carbon dioxide is substantially complete, signalling that the hydrolysis and decarboxylation have been substantially completed, the reaction mixture is cooled. The mixture may be cooled to a temperature between room temperature and about 100° C., although it is preferred that it be cooled to a temperature between about 40°–60° C. The mixture may then be treated with water. The layers are allowed to separate, and the layer containing the acid catalyst and the water is removed. This layer containing the catalyst can be re-used without further treatment by adding it to the next batch and distilling out water until the desired reaction temperature is attained. The remaining organic layer comprises the alkanoic acid. When the alkanoic acid is valproic acid, the recovered organic layer is a light brown liquid.

The alkanoic acid recovered at this step of the process is of sufficient purity for a number of uses. However, for most pharmacological applications a further purification step must be employed in order to obtain a colorless end product. Preferably, this final purification step comprises vacuum distillation of the alkanoic acid.

For other non-pharmacological applications, alternative purifications separation steps may be employed if desired. For example, the recovered organic layer may be washed with aqueous sodium chloride to remove traces of the catalyst that may be present in this layer. Also, if the acid catalyst is not to be recycled, the separated water layer may be washed with toluene in order to remove any alkanoic acid from this layer. The toluene layer is then combined with the crude alkanoic acid layer, and the reaction product may then be subjected to further purification steps, such as vacuum distillation.

The following examples are presented in order to more fully illustrate the process of the present invention:

Example 1

Valproic Acid.

A mixture of 70 g of p-toluenesulfonic acid monohydrate, 140 g of diethyl dipropylmalonate and 9 ml of water was heated to reflux in a flask equipped with a distillation column packed with Raschig rings. Ethanol was distilled as it formed and the pot temperature was maintained at 120°-155° C. by periodic addition of water to the pot. After 5 hours, 25 ml of water had been added and the evolution of ethanol had nearly stopped. The mixture was maintained at 140° C. for 18 hours and then was cooled and treated with 100 ml of water. The layers were separated to afford 72.2 g (87.8% yield) of valproic acid as a light brown liquid. The water layer was washed with 50 ml of toluene and the toluene was combined with the crude valproic acid layer. Vacuum distillation afforded a colorless valproic acid fraction (72 g, 87% yield) boiling at 132° C./28" Hg.

EXAMPLE 2

Valproic Acid.

A mixture of 38.6 ml of 70% methanesulfonic acid and 352.2 g of diethyl dipropylmalonate was heated to 135°-145° C. in a flask equipped with a distillation column packed with Raschig rings. After 1.5 hour, ethanol began to reflux in the distillation head. Ethanol was distilled as it formed and the pot temperature was maintained at 120°-145° C. by periodic addition of water to the pot. After 5 hours, additional ester (133 g) was added to the pot and the distillation of ethanol was continued. After 24 hours, the distillation of ethanol had ceased. The mixture then was cooled and treated with 50 ml of water. The layers were separated and the organic layer was washed with 100 ml of 5% sodium chloride solution to afford 257.6 g (90% yield) of valproic acid as a light brown liquid.

EXAMPLE 3

2-Methylhexanoic Acid.

A mixture of 40 g of p-toluenesulfonic acid monohydrate and 313 g of diethyl butylmethylmalonate was heated to 125°-135° C. in a flask equipped with a distillation column packed with Raschig rings. After 15 minutes, ethanol began to reflux in the distillation head. Ethanol was distilled as it formed and the pot temperature was maintained at 120°-126° C. by periodic addition of water to the pot. After 22 hours, the distillation of ethanol had ceased. The mixture then was cooled and treated with 70 ml of water. The layers were separated to afford 159.2 g (90.6% yield) of 2-methylhexanoic acid (99.8% pure by VPC).

While this invention has been described in a preferred embodiment, the present invention can be further modified within the spirit and scope of this disclosure. This description is therefore intended to cover any variations, uses, or adaptations of the invention using its general principles. Further, this description is intended to cover such departures from the present disclosure as come within known or customary practice in the art to which this invention pertains and which fall within the limits of the appended claims.

What is claimed is:

1. A process for production of alkanoic acids of the formula

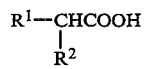

wherein $R^1$ is an alkyl group containing from about 2 to 10 carbon atoms, or a branched alkyl, cycloalkyl or aryl group containing from about 3 to 10 carbon atoms and $R^2$ is H or an alkyl group containing from about 1 to 10 carbon atoms, or a branched alkyl, cycloalkyl or aryl group containing from about 3 to 10 carbon atoms, the process comprising:

heating a reaction mixture comprising (1) a substituted malonic ester of the formula

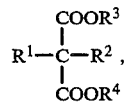

wherein $R^1$ and $R^2$ represent alkyl, branched alkyl, aryl or cycloalkyl groups as described above, and $R^3$ and $R^4$ represent lower alkyl groups, (2) water, and (3) an acid catalyst to a temperature sufficient to hydrolyze and decarboxylate the ester, said acid catalyst being at least partially soluble in the ester at temperatures above about 100° C. and being selected from the group consisting of arylsulfonic acids, alkylsulfonic acids and mixtures thereof, said water being limited to an amount insufficient for complete extraction of the acid catalyst from the ester to the water;

removing substantially all of the alcohol and carbon dioxide generated by the hydrolysis and decarboxylation from the reaction mixture including alkanoic acid and the catalyst by maintaining the reaction mixture at said temperature for a period of time sufficient to drive the hydrolysis reaction substantially to completion; and separating the catalyst from the alkanoic acid.

2. The process of claim 1, wherein the substituted malonic ester is an alkyl substituted malonic ester.

3. The process of claim 1, wherein the malonic ester is substantially hydrophobic.

4. The process of claim 1, wherein the acid catalyst is p-toluenesulfonic acid monohydrate, methanesulfonic acid or a mixture thereof.

5. The process of claim 1, wherein the alcohol is removed from the reaction mixture by distillation.

6. The process of claim 1, wherein the substituted malonic ester is diethyl dipropylmalonate or diethyl butylmethylmalonate.

7. The process of claim 1, wherein the total number of carbon atoms in $R^1$ and $R^2$ is not greater than about 16.

8. The process of claim 7, wherein the total number of carbon atoms in $R^1$ and $R^2$ is not greater than about 10.

9. The process of claim 1, wherein $R^3$ and $R^4$ comprise a methyl group or an ethyl group.

10. The process of claim 1, wherein the hydrolysis reaction is carried out a temperature between about 100°–155° C.

11. The process of claim 10, wherein said temperature is between about 120°–140° C.

12. The process of claim 1, wherein the reaction mixture is maintained at said temperature by periodic addition of water in said limited amount to the reaction mixture.

13. A process for production of alkanoic acids of the formula

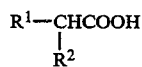

wherein $R^1$ is an alkyl group containing from about 2 to 10 carbon atoms, or a branched alkyl, cycloalkyl or aryl group containing from about 3 to 10 carbon atoms and $R^2$ is H or an alkyl group containing from about 1 to 10 carbon atoms, or a branched alkyl, cycloalkyl or aryl group containing from about 3 to 10 carbon atoms, and wherein the sum of the carbon atoms in $R^1$ and $R^2$ does not exceed about 16, comprising:

preparing a reaction mixture consisting essentially of a substituted malonic acid of the formula

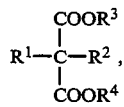

wherein $R^1$ and $R^2$ represent alkyl, branched alkyl, aryl or cycloalkyl groups as described above, and $R^3$ and $R^4$ represent lower alkyl groups; an acid catalyst, said acid catalyst being at least partially soluble in the ester at temperatures above 100° C. and comprising an arylsulfonic acid, an alkylsulfonic acid or a mixture thereof; and water, the water in the reaction mixture being limited to an amount insufficient for complete extraction of the acid catalyst from the ester to the water;

heating the reaction mixture to a temperature sufficient to hydrolyze and decarboxylate the ester;

maintaining the reaction mixture at said temperature by periodic addition of water in said limited amount to the reaction mixture, and continuing to heat the reaction mixture at said temperature for a period of time sufficient to remove substantially all of the alcohol and carbon dioxide generated by the hydrolysis reaction, thereby converting substantially all of the ester to alkanoic acid; and separating the catalyst from the alkanoic acid.

14. The process of claim 13, wherein the substituted malonic ester is one of diethyl dipropylmalonate and diethyl butylmethylmalonate, and the alkanoic acid is valproic acid.

15. The process of claim 13, further comprising the step of purifying the alkanoic acid by vacuum distillation.

16. The process of claim 13, wherein said reaction is carried out at a temperature between about 100°–155° C.

17. The process of claim 16, wherein the reaction temperature is between about 120°–140° C.

18. The process of claim 13, wherein the acid catalyst is one of p-toluenesulfonic acid monohydrate, methanesulfonic acid and mixtures thereof.

19. The process of claim 13, wherein the malonic ester is substantially hydrophobic.

20. The process of claim 13, wherein the alcohol is removed from the solution by distillation.

21. The process of claim 13, wherein $R^3$ and $R^4$ comprise a methyl group or an ethyl group.

22. The process of claim 13, wherein the reaction mixture comprises between about 1–200 mole % acid catalyst.

23. The process of claim 22, wherein the reaction mixture comprises between 15–20 mole % acid catalyst.

24. The process of claim 13, wherein the preparing, heating and maintaining steps all take place in a single reaction vessel.

25. A process for preparing valproic acid comprising:
preparing a reaction solution in a reflux flask equipped with a distillation column, said reaction solution consisting essentially of a substituted malonic ester selected from the group consisting of diethyl dipropylmalonate and dimethyl dipropylmalonate, an acid catalyst selected from the group consisting of an arylsulfonic acid, an alkylsulfonic acid and mixtures thereof, and water, the acid catalyst being at least partially soluble in the ester at temperatures above 100° C., and the water being limited to an amount insufficient for complete extraction of the acid catalyst from the ester to the water;

heating the reaction mixture to a temperature sufficient to hydrolyze and decarboxylate the ester, said temperature being between about 100°–155° C.;

maintaining the reaction mixture at said temperature by periodic addition of water in said limited amount to the flask, and continuing to heat the reaction mixture at said temperature for a period of time sufficient to remove substantially all of the ethanol and carbon dioxide generated by the hydrolysis and decarboxylation of the ester, thereby converting substantially all of the ester to valproic acid;

separating the catalyst from the valproic acid; and
purifying the valproic acid.

26. The process of claim 25, wherein the valproic acid is purified by vacuum distillation.

27. The process of claim 25, further comprising the steps of allowing the hydrolyzed reaction solution to cool, and treating the cooled mixture with water prior to separating the catalyst from the valproic acid.

28. The process of claim 25, wherein the acid catalyst is one of p-toluenesulfonic acid monohydrate, methanesulfonic acid and mixtures thereof.

* * * * *